(12) United States Patent
Elezzabi

(10) Patent No.: US 9,550,069 B1
(45) Date of Patent: Jan. 24, 2017

(54) SYSTEM AND METHOD FOR FEMTOSECOND LASER PULSE TREATMENT OF MACULAR DEGENERACY, RETINAL DRUSEN TREATMENT, AND COLLOIDAL BODIES OF RETINA REMOVAL

(71) Applicant: Abdulhakem Elezzabi, Edmonton (CA)

(72) Inventor: Abdulhakem Elezzabi, Edmonton (CA)

( * ) Notice: Subject to any disclaimer, the term of this patent is extended or adjusted under 35 U.S.C. 154(b) by 76 days.

(21) Appl. No.: 14/638,573

(22) Filed: Mar. 4, 2015

Related U.S. Application Data

(60) Provisional application No. 61/966,917, filed on Mar. 6, 2014.

(51) Int. Cl.
*A61N 5/067* (2006.01)
*A61N 5/06* (2006.01)

(52) U.S. Cl.
CPC ....... *A61N 5/0613* (2013.01); *A61N 2005/067* (2013.01)

(58) Field of Classification Search
None
See application file for complete search history.

(56) References Cited

U.S. PATENT DOCUMENTS

2004/0254567 A1* 12/2004 Holz ............... A61F 9/008
606/4
2014/0194860 A1* 7/2014 Dick .............. A61F 9/00825
606/6

* cited by examiner

*Primary Examiner* — Brian T Gedeon
(74) *Attorney, Agent, or Firm* — Miller Thomson LLP; Tai W Nahm

(57) ABSTRACT

There is disclosed a system and method for irradiating extracellular macular deposits through a cornea of an eye utilizing laser pulses. In an embodiment, the method comprises generating laser pulses of between about 1 femtosecond to 1,000,000 femtoseconds in a wavelength range from about 200 nanometers to 30 micrometers; and irradiating the extracellular macular deposits with the laser pulses for a preset temporal duration, energy, wavelength, spectral distribution, energy fluence, and power density. In an embodiment, the laser source generates a laser pulse in the range of about 0.001 nJ to 100 mJ of optical energy. By focusing the laser at a depth targeting extracellular macular deposits, the irradiating laser pulse is configured to ionize, remove, deplete, denature, and destroy the extracellular macular deposits without damaging the retinal pigmented epithelium cell membrane or mascula.

19 Claims, 8 Drawing Sheets

SYSTEM AND METHOD FOR FEMTOSECOND LASER PULSE TREATMENT OF MACULAR DEGENERACY, RETINAL DRUSEN TREATMENT, AND COLLOIDAL BODIES OF RETINA REMOVAL

FIELD

The present disclosure relates to a system and method for treatment of age-related macular degeneracy, retinal drusen treatment, colloidal bodies of retinal removal utilizing femtosecond laser pulses.

BACKGROUND

Age-Related Macular Degeneration (AMD) is a highly pervasive degenerative condition of the retina. AMD currently affects approximately one million Canadians; and the likelihood of developing AMD for people over the age of 75 years of age is 1 in 4 [1]. The initial symptoms present themselves as blurred or distorted vision and as the disease progresses the vision worsens as the central area of vision degenerates to the point of total blindness. There are two distinct stages to the progression of the condition [2]. The first stage of AMD, known as dry AMD, is characterized by the formation of lipoprotein deposits called drusen. The drusen develop on the outer layer of the retina between the Retinal Pigment Epithelium (RPE), the last layer of the retina, and the Bruch's membrane, the first layer of the choroid. These drusen cause cellular stress on the RPE cells leading to increased photoreceptor death. Eventually, dry AMD progresses to the final stage of the condition known as wet AMD where blood vessels of the choroid extend into the retina. This rapid neovascularization of the retina leads to leaky blood vessels that exude blood into the retina leading to more rapid photoreceptor death. The wet stage, in particular, results in total vision loss, thus, deemed more severe than the dry form. There is strong evidence to suggest that all reported cases of wet AMD occur due to the progression of the disease from the dry AMD stage. Thus, the most efficient way of preventing the severe wet form of AMD is to treat the condition while in the dry stage, hindering the progressing of the disease past the less severe stage.

To date, extensive research on the treatment of AMD using laser technology has been performed. Previous attempts to treat AMD using laser therapy include photodynamic therapy and photocoagulation treatment [2]. In photodynamic therapy, a photosensitizer is administered and then excited with a laser source. Due to the excitation of the photosensitizer material, it stimulates the production of free radicals that induce cell death of the desired tissue. In the treatment of AMD, the photosensitizer is injected into the leaky blood vessels where it is absorbed by the endothelial cells of the blood vessels. Once the photosensitizer is excited, cell death is induced in the endothelial cells, slowing the progression of the exudative blood vessels within the retina. In photocoagulation the laser is used to cauterize the leaky blood vessels in the retina. These previous methods of treatment are both hindered by the same shortcomings: lack of specificity and targeting only the final stage of the condition, when a significant amount of vision loss has already occurred. Both forms of treatment target the exudative vessels in the retina but are characterized by large-scale collateral damage within the retina. While the laser in photodynamic therapy can be targeted at certain areas of the retina, the photosensitizer is not tissue selective in which cells uptake the sensitizer. Thus, any cell containing the photosensitizer that the laser beam hits will be exposed to free radicals and go through apoptosis; leading to excessive cellular death around the desired target. Photocoagulation leaves large-scale lesions on the retina, and a potential side effect of these lesions is the loss of peripheral vision. Therefore, an attempted treatment for the loss of central vision can potentially lead to the loss of the patient's peripheral vision. To date, there has not been a successful treatment developed to prevent the progression of AMD by targeting the early dry stages of the condition.

In recent years, researchers have made some advances in the treatment of AMD. More specifically, Dr. Guymer et al. at the Macular Research Unit, Centre for Eye Research at the University of Melbourne, Royal Victorian Eye and Ear Hospital, Melbourne, Australia discovered that by exposing the macula to nanosecond (billionth of a second long) laser pulses, significant macular regeneration was observed. According to this Australian group, the laser treatment eliminated drusen in the treated eye and in so doing, reverses the degenerative process of AMD and save patients' sight. Fourteen patients have been followed to the 6-month mark. Of these, 10 patients had improved visual function or drusen removal. The researchers attribute the regeneration mechanism to the improvement of the transport properties of the Bruch's membrane hydraulic conductivity where the laser radiation triggers retinal pigmented epithelial cells to change. The Australian group asserts that the key to such a treatment is the use of nanosecond-long laser pulses to cause retinal pigmented epithelium cells to be destroyed without damaging adjacent health cells.

The Australian group claim to be blasting cells within the RPE layer using a nanosecond laser. This blasting of the retina induces the formation of micro-bubbles within the RPE cells causing cell death without rupturing the cell membrane, in order to stimulate rejuvenation of the RPE layer. The Australian group report not only improvement of the retinal function in AMD patients, but also regression of the disease [3]. Within the claims of their retinal rejuvenation mechanism they state that damaging the cells within the RPE induces a reparative cellular response, which results in improvement of the transport capabilities of the Bruch's membrane. Within the claims of a patent application for retinal rejuvenation it is stated that the group is killing RPE cells, inducing the migration of RPE cells into the targeted region and stimulating an improvement in the transport capabilities of the Bruch's membrane [3]. In a different publication it is stated that the laser pulses stimulate a natural cellular reparative process in the RPE cells, leading to the RPE functional rejuvenation without inducing cell death [4]. Thus, it is not clear whether the reparative process kills the cells or not. However, both of these suggested tissue repair processes are unlikely, as it is an established fact that the RPE cells of the central retina have no inherent biological rejuvenation systems and they do not reproduce [5-8]. This leads to the conclusion that the rejuvenation mechanism is still poorly understood, thus, it is still not clear if this treatment mechanism results in the regression of the disease.

Furthermore, the claim that nanosecond-long laser pulses can deliver a significant amount of energy without heat delivery, and thus thermal damage, is likely incorrect. Nanosecond laser pulse will damage healthy cells and the neuro-retina layer as the energy is deposited over a long time (longer than the electron energy relaxation time).

Therefore, what is needed is an improved system and method for laser-based treatment that addresses some of the limitations in the prior art and renders laser-AMD treatment to be more effective.

SUMMARY

The present disclosure relates to a system and method for utilizing femtosecond laser pulses to treat and destroy drusen for patients with age-related macular degeneracy (AMD), retinal drusen treatment, and colloidal bodies of retina removal. An exemplary system incorporating a 10 fs laser pulse and slit lamp is illustrated in FIGS. 1(A) and 1(b).

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION

The present disclosure relates to a system and method for utilizing femtosecond laser pulses to treat and destroy drusen for patients with age-related macular degeneracy (AMD), retinal drusen treatment, and colloidal bodies of retina removal.

In recent years, many laser based medical therapeutic, imaging and diagnosis devices have been developed. This makes the understanding of laser-tissue interaction processes increasingly important. The parameters that influence the quality of the laser-tissue interaction are the ionized electron density, the temperature change in the focal volume, the shockwave expansion, and cavitation bubble formation within the tissue [9-12]. These conditions determine the spatial extent of the tissue disruption. In order to control the extent of this disruption, it is required to tune the laser pulse duration, laser peak power, energy of the laser beam, pulse wavelength, and the pulse repetition rate.

With the advent of femtosecond laser sources, the physics of laser-tissue interaction has been adjusted due to the much shorter time frame of interaction, the significantly higher power delivered to the tissue, and the significantly lower deposited energy. Ultrashort laser pulses last in between 5 femtoseconds (5×10−15) to 100 picoseconds (100*10−12) per pulse. Femtosecond laser pulses can reach extremely high peak powers in the range of 1 MW to 100 GW per pulse. An extremely high peak power, such as these, is emitted during an extremely short time, giving rise to key ultrafast nonlinear interaction. Since these processes are nonlinear, they occur only when a certain energy threshold is reached, and only across the location of the peak intensity of the laser focal spot, which is much smaller than the laser diffraction-limited full width half maximum (FWHM) spot.

Figure 1A:
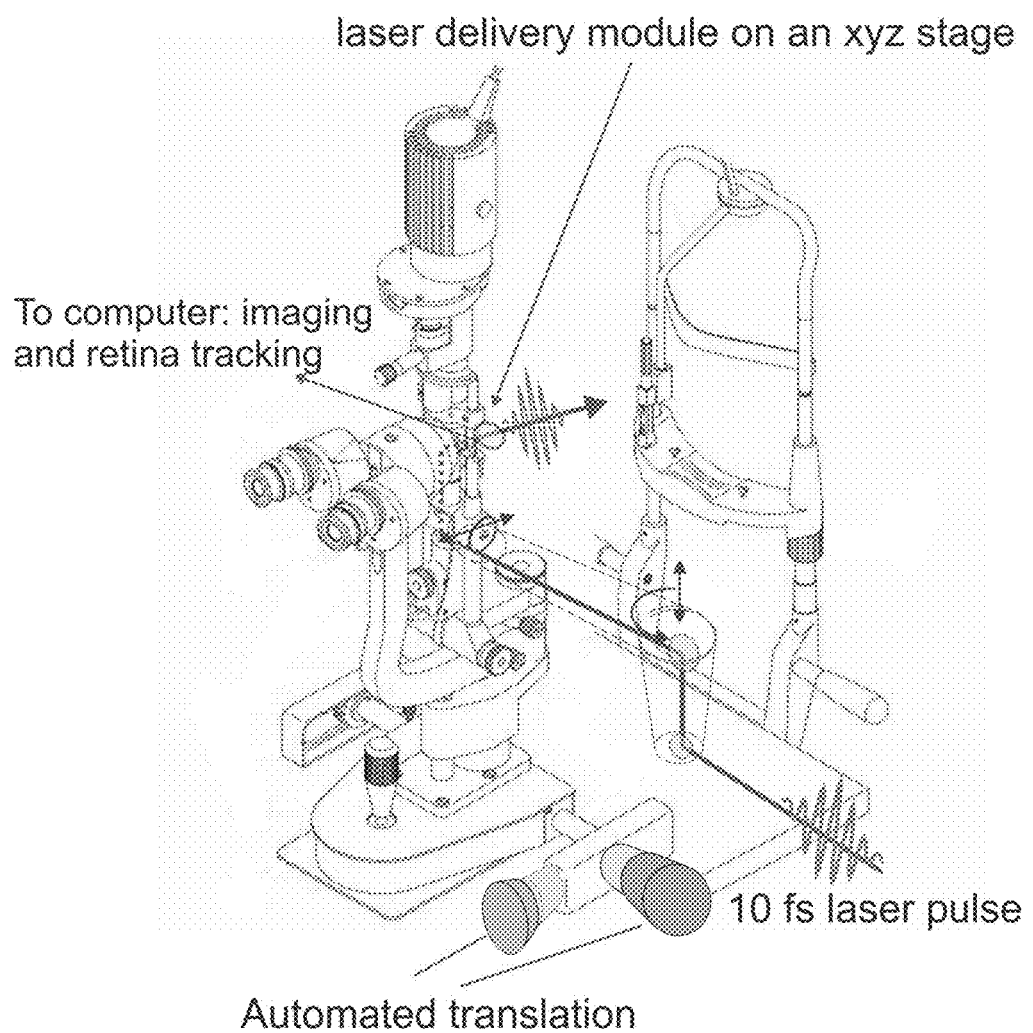
FIG. 1(a) shows an illustrative apparatus for delivering femtosecond laser pulse treatment for age-related macular degeneration in accordance with an embodiment.
Figure 1B:
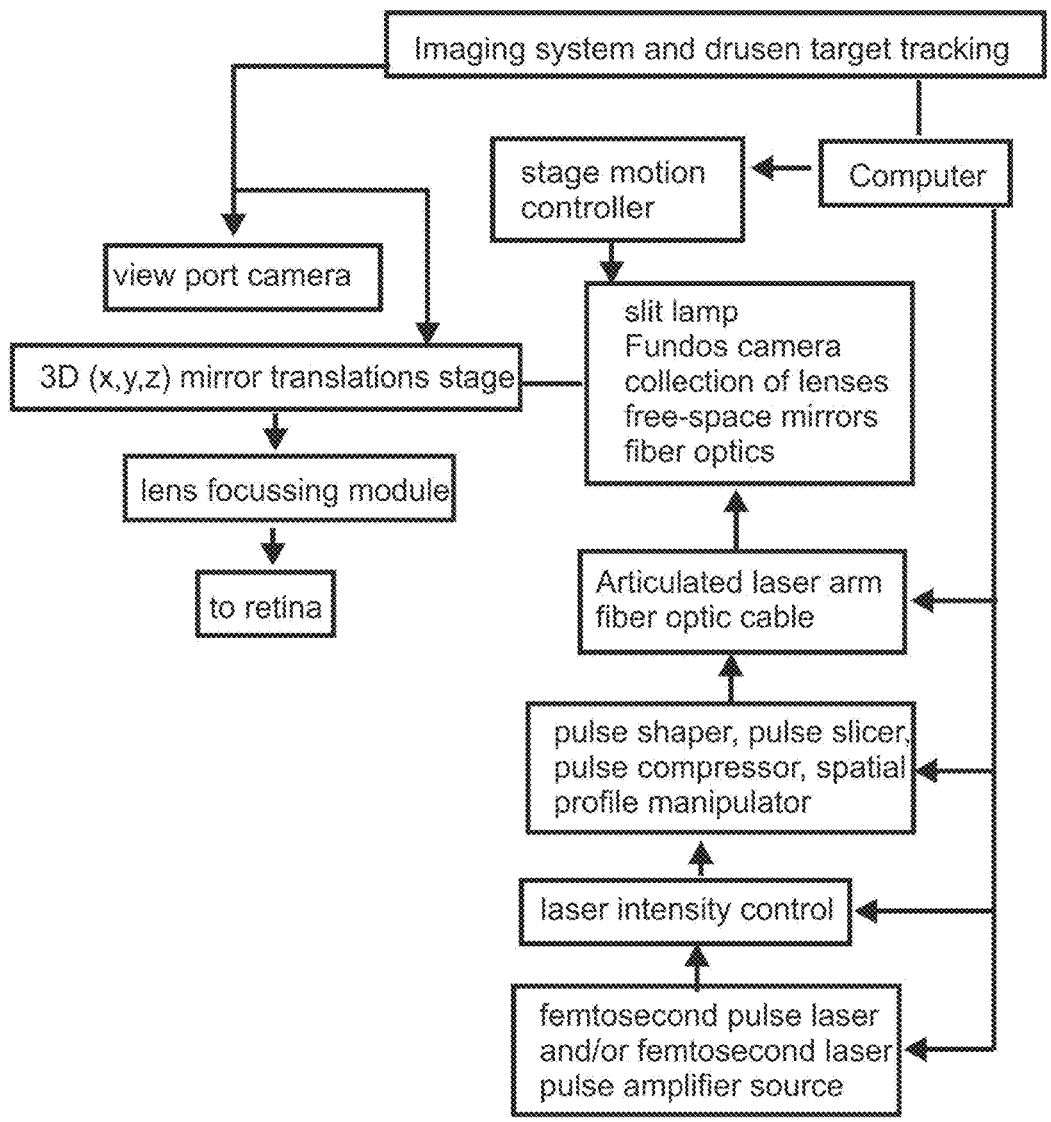
FIG. 1(b) shows a schematic flow chart of a method in accordance with an embodiment.

By way of example, an exemplary system and method incorporating a 10 fs laser pulse and slit lamp is illustrated in FIGS. 1(a) and 1(b), respectively.

When a laser beam is focused onto biological tissue, the material absorbs the irradiation either through single photon absorption or nonlinear absorption, depending on the laser wavelength, laser intensity, and laser pulse duration [9-17]. When the pulse duration is on the order of femtoseconds, the pulse's high energy density induces multi-photon absorption. This process initiates multiphoton ionization and break down of the tissue.

Figure 4:
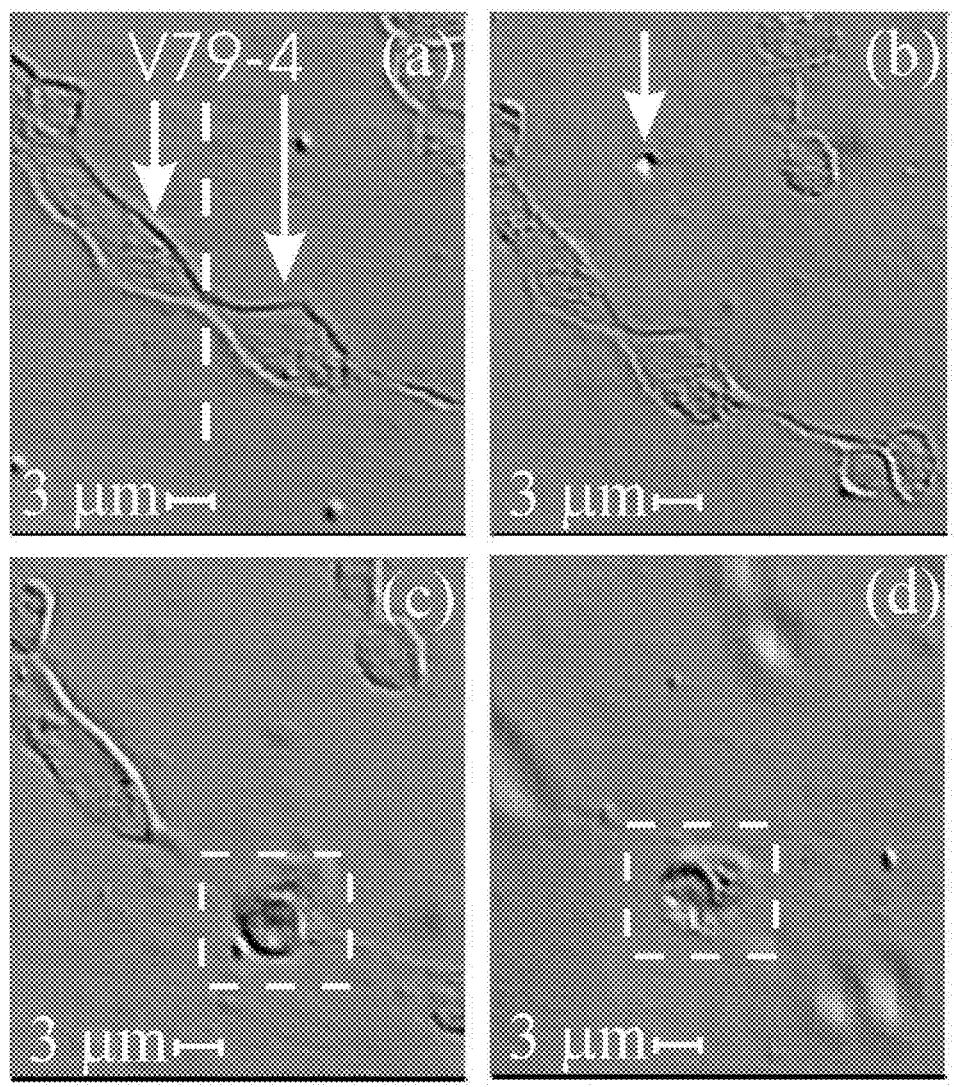
FIG. 4 shows an illustration of isolation of living fibroblasts(V79-4)

FIG. 4 contrasts multi-photon absorption and single photon absorption processes. In FIG. 4, during multi-photon absorption, three photons with an energy of 1.55 eV (800 nm) are needed to promote an electron from its lower energy state to the upper energy state. In single photon absorption, a single photon with energy of 4.65 eV (266 nm) would be required to excite the electron to the same upper state. The benefit of multi-photon absorption compared to single photon absorption is rooted in the lower energy required to elicit material ablation, and the ability to localize cellular disruption. The lower energy threshold required for photo-disruption results in less excessive energy available to be funneled into adverse side effects such as shockwave and cavitation bubble formation, in turn, significantly reducing the spatial disruption [9-12]. The longer wavelengths also allow deeper penetration of the laser pulses into the tissue [14-16]. Furthermore, processes that depend on multi-photon absorption are not activated by scattered light since scattered photons do not have the temporal and spatial coherence necessary for multi-photon excitation; further reducing spatial disruption [13,15].

Another important property of femtosecond laser pulses is their ability to deliver extremely high power to the tissue, while having low energy per pulse. Pulse energy is proportional to the pulse power (inversely proportional to the pulse duration). Hence, for constant pulse power, the energy deposited into the material is substantially lower for femtosecond laser pulses compared to nanosecond or picosecond laser pulses. For example, 10 GW peak power delivered by laser pulse duration of 10 ns will deposit 100 J of energy to a tissue, whereas 10 GW peak power delivered by laser pulse duration of 100 fs will deposit 1 mJ of energy to the tissue; which is 100,000 times less than for a nanosecond pulse. For near-infrared femtosecond laser pulse excitation, multiphoton absorption occurs on the time scale corresponding to the duration of the pulse. This exposure time is much shorter than the time scale of electron-ion (or neutral atom) energy transfer and the thermal diffusion time. Thus, energetic electrons are created locally and induce tissue breakdown before they can transfer their energy to the surroundings, meaning that the electronic excitation is efficiently decoupled from the thermal relaxation process. This results in a nearly insignificant heat deposition within the tissue. Neev et al. [18] used infrared camera to determine the temperature rise at the surface of ablated dentin tissue irradiated with femtosecond laser pulses (350 femtoseconds) at a repetition rate of 10 Hz. The maximum observed temperature rise was 3.9° C. above room temperature [18]. Vogel et al. [9] used simulations to estimate the temperature rise from the application of a single femtosecond laser pulse (100 femtoseconds) in water. He determined that since the laser pulse duration was shorter than the relaxation time of the molecules, the temperature rise is given by $$\Delta T = \varepsilon/(\rho_0 C_p) \Delta T = \frac{\varepsilon}{\rho_0 C_p} \quad (1)$$

Where $\varepsilon$ is the volumetric energy density, $\rho 0$ is the density of water, and $C_p$ is the specific heat capacity (4.184 J/K·g). This equation represents the change in temperature within the focal volume with respect to the deposited energy density. As both the density of water and the heat capacity are constants, the change in temperature is linearly proportional to the deposited volumetric energy density. As an example, for 1 J/cm−3 deposited, the temperature rise for 1 cm3 of water is calculated to be $\Delta T=0.2$ K above room temperature. The combination of multiphoton absorption processes and the minimal temperature rise within the tissue resulted in the ability to change the structure with a resolution below the diffraction limit.

Notably, for femtosecond laser pulses, the extent of the spatial disruption due to the formation of shockwaves and cavitation bubbles are minimal. The strength of these effects depends on the deposited laser energy, where an excess of energy deposited is funneled into increasing the disruptive forces of shockwave and cavitation [9-10]. Studies have shown that pressure amplitudes decrease with shorter pulse durations, as shorter pulses have less excessive energy and thus a smaller amount of energy is funneled into shockwave formation. Moreover, less funneled energy also induces faster shockwave decay time, which in turn reduces the pressure amplitude as a function of distance. Thus, the combined effects of low thermal stress in the material and small shockwave and cavitation formation decrease the spatial extent of tissue disruption leading to the ability to perform high accuracy tissue ablation.

Effectiveness of Femtosecond Pulse Laser Treatment of AMD

Over the past eight years, the inventor and his research team have been performing laser nanosurgery and transfection on living embryos and single cells at the Ultrafast Optics and Nanophotonics Laboratory in the Department of Electrical and Computer Engineering, University of Alberta. More recently, the research team have been using ultrafast laser pulses known as femtosecond (millionth of a billionth of a second-long pulses) infrared pulses. This work has received international recognition and has been hailed as a breakthrough in laser-single cell surgery. In the process, the team has invented a unique tool enabling non-invasive manipulation of living biological cells. The team has developed physical models describing laser-bio-matter interaction mechanisms and has identified the parameters and operating regime needed for nanosurgery of cells.

Based on this research, the inventor has demonstrated that nanosecond laser pulses are inefficient in energy delivery and do result in significant delivery of heat (burning of cells), accompanied by strong mechanical stress and shock waves leading to rupturing of healthy cells as well as the unhealthy ones (i.e. there is no distinction between the cells because the laser damage spot is very large). The inventor has further shown that the conclusions reached by earlier researchers concerning the interaction of nanosecond laser pulses at a 500 nm wavelength with retinal pigmented epithelial cells for AMD treatment are likely incorrect, as it is likely that incorrect laser parameters (pulse duration, wavelength, and energy density).

Figure 2:
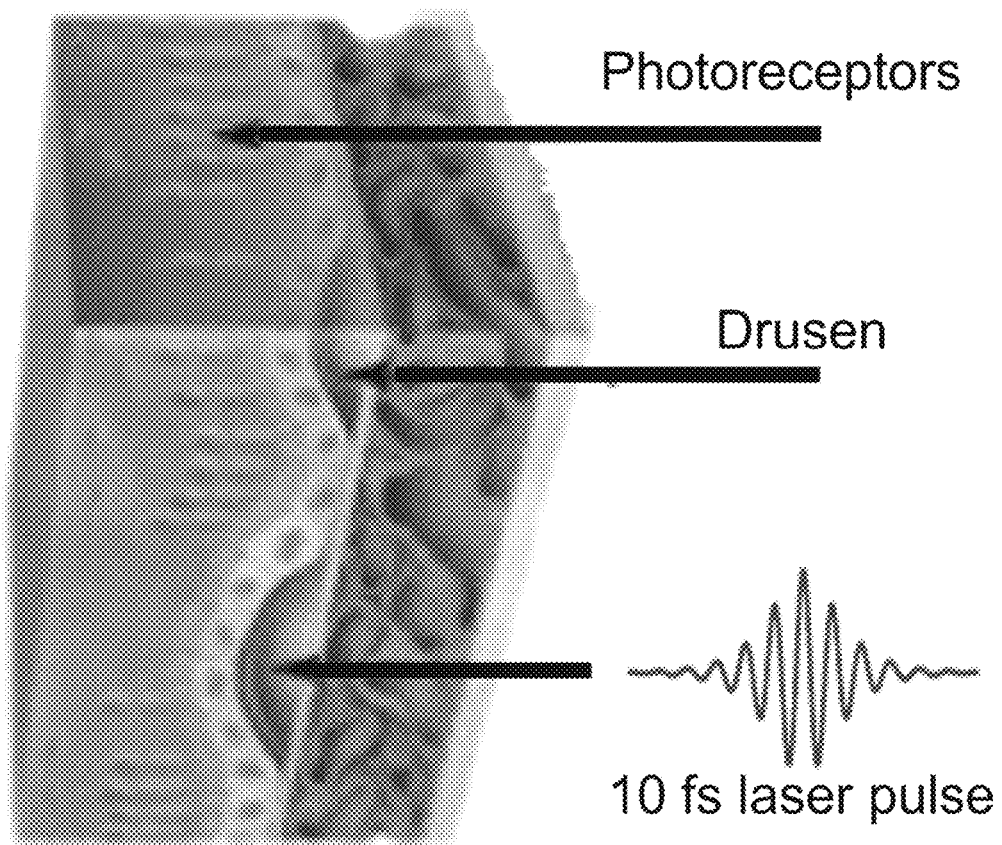
FIG. 2 shows an illustration of femtosecond laser pulses being directed to cells with drusen without depositing energy or damaging the neuro-retina.

Through further research and experimentation, the inventor has now recognized that femtosecond pulse technology would be superior to nanosecond laser pulses for the treatment of AMD, retinal drusen treatment, colloidal bodies of retinal removal because femtosecond pulses can effectively isolate and penetrate cells for delivery of nanoparticles, and perform 3D nanoscale surgery in virtually any type of cell. Advantageously, the use of 10-femtosecond laser pulses, operating for example and not by way of limitation at common laser wavelengths of 800 nm or 1550 nm wavelengths, may lead to much improvement in laser-AMD treatment (FIG. 2).

Femtosecond Laser Pulse Interaction with Biological Materials

The laser light can be focused beyond cellular structures and localized to a region of interest without disrupting cellular material above or below the laser focal spot. Only at the focus will biological material be laser pulse ablated, either for dissection, excision or permeabilization, through a linear or nonlinear process interaction.

As recognized by the inventor, femtosecond plasma mediated pulse ablation is a very efficient process that is statistically reproducible with defined ablation thresholds. This is in contrast to plasma mediated pulse ablation using longer pulse durations (nanosecond or picosecond long, where seed electrons are produced via thermionic emission of impurity electrons Fluctuations in the impurity density result in varying ablation threshold values, making optical breakdown a statistically irreproducible process.

The benefit of femtosecond laser pulses over longer pulse durations is inherent in the lower threshold energy required to elicit ablation and the ability to localize the cellular and sub-cellular disruption to a high (typically on the order of sub-micron) spatial resolution. Both of these factors are intrinsically coupled, since the lower threshold energy means that less energy is available to be funneled into adverse side effects such as shockwave and cavitation bubble formation, which are known to increase the spatial extent of tissue damage. Multiphoton absorption is the initiator of the laser pulse ablation of biological material. Through nonlinear absorption, the simultaneous absorption of many photons leading to a quasi-ionized electrons.

Femtosecond Laser Pulses for AMD Treatment

Taking advantage of the low spatial disruption and the ability to manipulate structures smaller than the diffraction limit using femtosecond laser pulses gives great potential for the development of a novel treatment mechanism for dry AMD. Using femtosecond laser pulses it will be possible to target and destroy the drusens that characterize dry AMD without disrupting any surrounding retinal tissues. Thus, preventing the progression of the disease past the early stages of the dry form, and preserving the patient's vision.

In an embodiment, a suitable femtosecond laser treatment system includes a functional slit lamp customized for use in conjunction with a femtosecond laser delivery system. A coupling system is designed to deliver the laser beam from its source into the slit lamp, which is precisely aimed onto the drusens below the patient's retina. This is achieved by utilizing a custom laser beam articulating arm that will guide the laser beam from the source to the slit lamp pathway. Femtosecond plasma mediated pulse ablation is a very efficient process that is statistically reproducible with defined ablation thresholds. This is in contrast to plasma mediated pulse ablation using nanosecond pulse durations, where seed electrons are produced via thermionic emission of impurity electrons (also known as background or defect density). For nanosecond laser ablation, fluctuations in the impurity density result in varying ablation threshold values, making optical breakdown a statistically irreproducible process.

In an embodiment, a suitable femtosecond laser is a compact Ti: Sapphire femtosecond laser source manufactured by Femtolasers (Vienna, Austria)), capable of delivering 20-40 femtosecond laser pulses at a pulse energy of ~20 nJ. The laser operates within the infrared region with a central wavelength of 800 nm. The energy density is adjusted accordingly, from patient to patient, in order to precisely select the optimal parameters to ablate the drusens, while minimizing damage to surrounding cells.

Additional components included in the design improve automation and sensitivity of the laser focus. For example, a high-speed adaptive optic varifocal device to control the focus depth during the laser ablation procedures. An automated aiming and laser targeting system may also be incorporated into the design in order to improve accuracy in delivery of the laser. This may be achieved by incorporating a CCD camera into the slit lamp, which is integrated with an automatic positioning system that will track the location of the drusens inside the patient's eye. The operator is then able to select the locations of the drusens, and command the computer to destroy them. The computer may be controlling a motorized mirror in order to precisely direct laser pulses at the selected locations. This technique dramatically improves the targeting precision of the device, and significantly reduce the probability of human error from occurring. Such positioning and targeting systems may be based on commercially available systems, commonly used in laser eye surgery procedures such as LASIK, and further modified as necessary for delivery of the laser to the inner back of the eye where the target treatment site is located.

Through harnessing the unique laser-tissue interaction properties of a femtosecond laser, potential positive impact in the lives of individuals affected by this disease is substantial.

In addition to the well-defined ablation thresholds for femtosecond laser pulses, using near infrared (NIR) wavelengths increases the plasma formation efficiency, since both the plasma absorption coefficient and cascade ionization rate are proportional to the square of the excitation wavelength. Therefore, a shift in the excitation wavelength from the visible (i.e. 532 nm) to NIR (i.e. 800 nm) increases the production rate of ionized electrons. Results have shown that cascade ionization is the more dominant process for creating ionized electrons. As long as seed electrons are created via multiphoton absorption, cascade ionization will produce more 'lucky electrons' than multiphoton absorption alone. For longer pulse durations (i.e. nanoseconds), seed electrons for cascade ionization are produced through thermionic emission. A rapid rise in the electron density occurs only when the optical breakdown irradiance is reached. Which is much easier to reach using femtosecond laser pulses than nanosecond laser pulses.

Laser Pulse Induced Heat Stress

The accumulation of heat and the rise in temperature during femtosecond mediated plasma ablation has been an active area of research. Generally the temperature rise is smaller for femtosecond laser pulses (due to the lower threshold energy for ablation) than for longer pulse durations. The temperature rise at the front surface of ablated dentin tissue irradiated with femtosecond laser pulses (100 femtoseconds) at a repetition rate of 10 Hz is very small. The maximum observed temperature rise was 2° C. above room temperature (23° C.).

Examples of Inventor's Research on Femtosecond Laser Pulse Interaction with Cells:

To illustrate the important implications of using femtosecond-long laser pulses for AMD treatment, below are some examples of other relevant applications. Since 2004, the inventor has been collaborating with cell and developmental biologists to demonstrate the use of femtosecond laser pulses to introduce, remove, and modify molecules and cellular material within the cellular environment.

FIG. 2 depicts membrane surgery on a live mammalian cell, in which the bright spot represents the focused laser pulse. In this illustration, a 10 Femtosecond laser pulse is delivered directly to the cells with drusen, without depositing energy or damaging the neuro-retina.

Here, energy is deposited beyond the frontal neuro-retina and energy is localized only in the drusen where multiphoton absorption and avalanche breakdown take place. Therefore, the neuro-retina cannot be damaged since the energy density is low for nonlinear absorption to take place. Several dissection cuts were made along the short and long axes of the cell. The cell maintained morphological integrity during and after surgery without evidence of collapse or disassociation.

Figure 3:
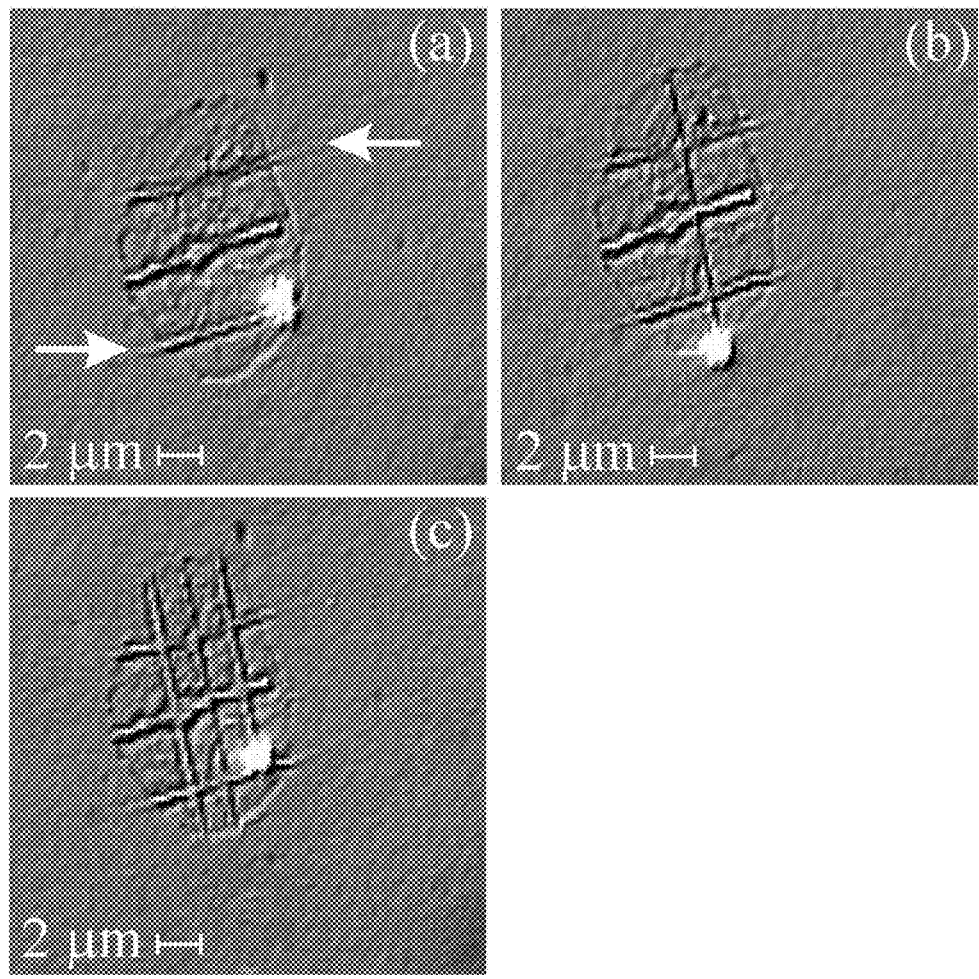
FIG. 3 shows an illustration of membrane surgery of a living Madin-Darby canine kidney (MDCK) cell using a femtosecond-pulsed laser.

Now referring to FIG. 3, shown is an illustrative membrane surgery of a living Madin-Darby canine kidney (MDCK) cell using a femtosecond-pulsed laser. The arrows in FIG. 3 represent the dissected extracellular matrix that anchors the cell to its substrate. Surgical incisions were made along the (a) short and (b), (c) long axes of the cell. Cell maintained morphology after the laser surgery. Scanning the focused laser spot around the contour of the cell allows single-cell isolation.

FIG. 4 shows isolation of living fibroblasts (V79-4). The arrows in (a) identify two cells tethered together by a focal adhesion. When the cells were scanned relative to the dissection interface (indicated by the dotted line), the focal adhesion was removed, resulting in isolation of a single cell from its adjoining partner. This cell can be observed in (c) and (d), curled and liberated from the substrate.

We also demonstrated nanosurgery on living embryonic cells. Using zebrafish as our animal model system, femtosecond laser pulses were used to transiently permeabilize blastomere cells for delivery of exogenous material, including fluorescent probes, quantum dots, and plasmid DNA.

Figure 5:
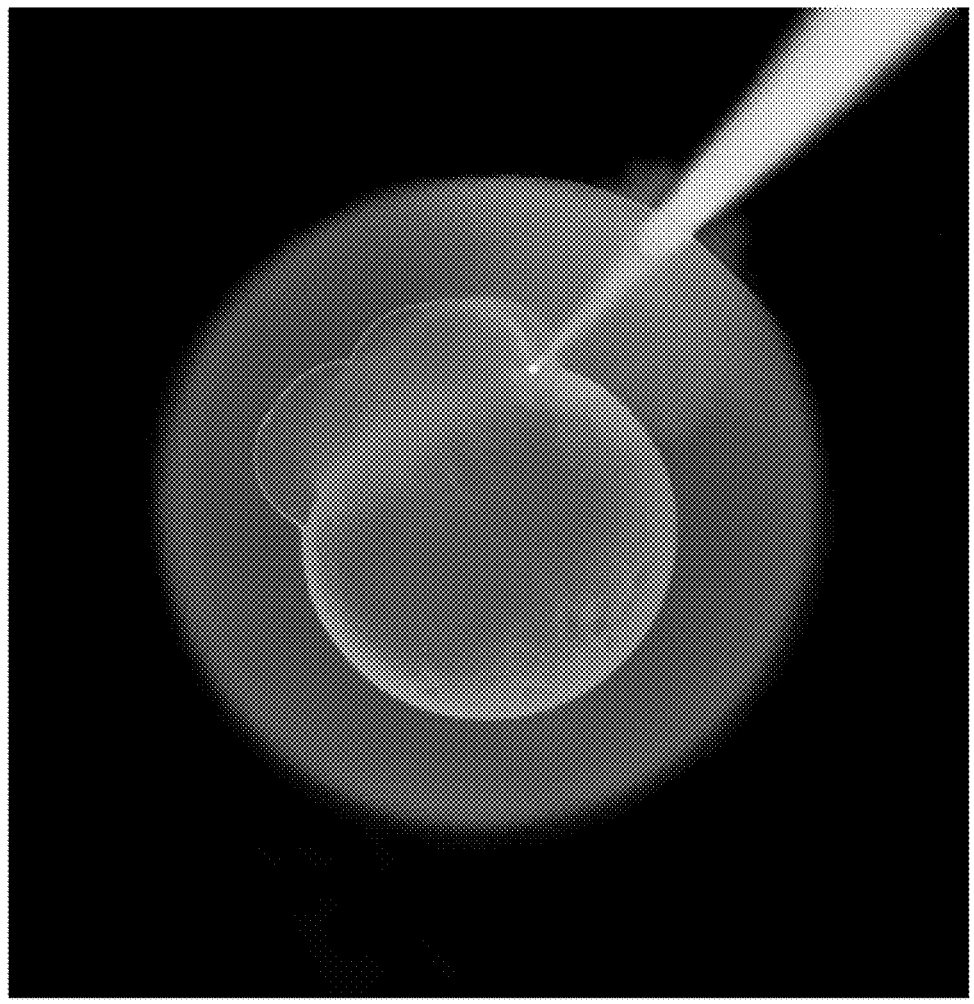
FIG. 5 shows an example of 3D-embryo nanosurgery.

Now referring to FIG. 5, shown is a depiction of 3D embryo nanosurgery within living embryonic cells utilizing a permeabilization method. Surrounding the developing embryo is a non-cellular layer, known as the chorion, which protects the embryo from the environment. Femtosecond laser pulses were focused beyond the chorion (the outer layer) and localized near or on the blastomere cells. With this method, the chorion remained intact. In FIG. 4, femtosecond laser pulses were focused beyond the chorion onto the embryonic cells.

Figure 6:
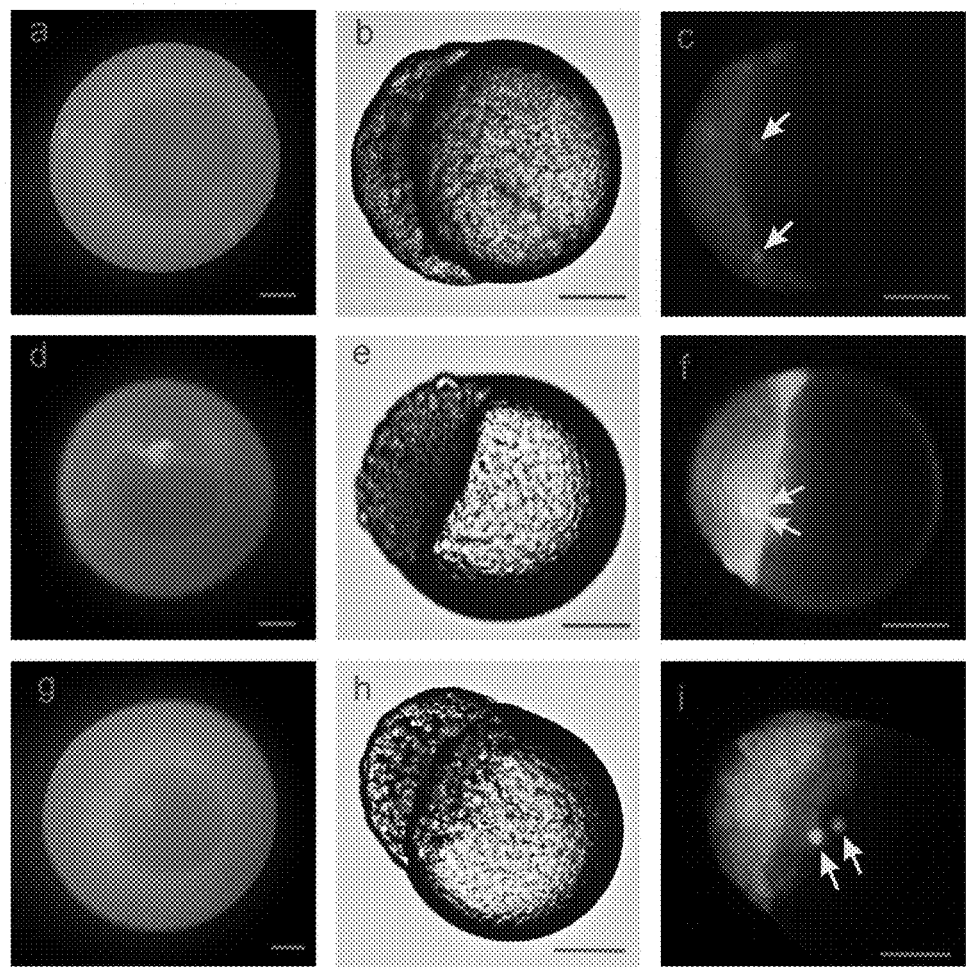
FIG. 6 shows an example of Zebrafish embryos at varying developmental stages permeabilized in the presence of a fluorescent probe.

FIG. 6 depicts material delivery into zebrafish embryos. In this series of photographs, zebrafish embryos are shown at varying developmental stages permeabilized in the presence of a fluorescent probe. In the first column, photographs (a), (d), (g) show fluorescence images in which embryos were initially bathed in the fluorescent probe to allow the dye to diffuse into the region between the chorion and embryo. The creation of transient pores was required for intracellular delivery because the probe could not permeate into the blastomere cells.

The second column photographs (b), (e), (h) show bright field images. Targeting laser pulses to a location near the blastomere cells, transient pores were formed, exposing the extracellular environment to the intracellular space. The pores were utilized as delivery pathways to introduce a fluorescent reporter molecule into the blastomere cells.

After removal of the chorion, photographs (c), (f), (i) show intracellular accumulation of the fluorescent probe was observed in the embryonic cells. Arrows represent the precise location where transient pores were formed.

Streptavidin-conjugated quantum dots and plasmid DNA were also introduced into zebrafish blastomere cells via transient pores. FIG. 6(a) depicts quantum dot fluorescence in a 2-cell stage zebrafish embryo. After rearing the embryo just past germ-ring stage (~6 hours), quantum dot fluorescence was still observable in the embryonic cells, as in (b). The larvae presented in (c), (d), (e), and (f) were transiently permeabilized at the early- to mid-cleavage stage (when the embryo ranges from two cells to eight or 16 cells) in the presence of a plasmid construct expressing enhanced green fluorescent protein (EGFP). Rearing embryos to 24 hours post-fertilization, expression of the DNA construct was observed along the zebrafish gut, floor plates, and in the somites and tail cells of the larvae. Such widely distributed expression indicates the plasmid was introduced through the laser-induced transient pores with resulting EGFP production.

Figure 7:
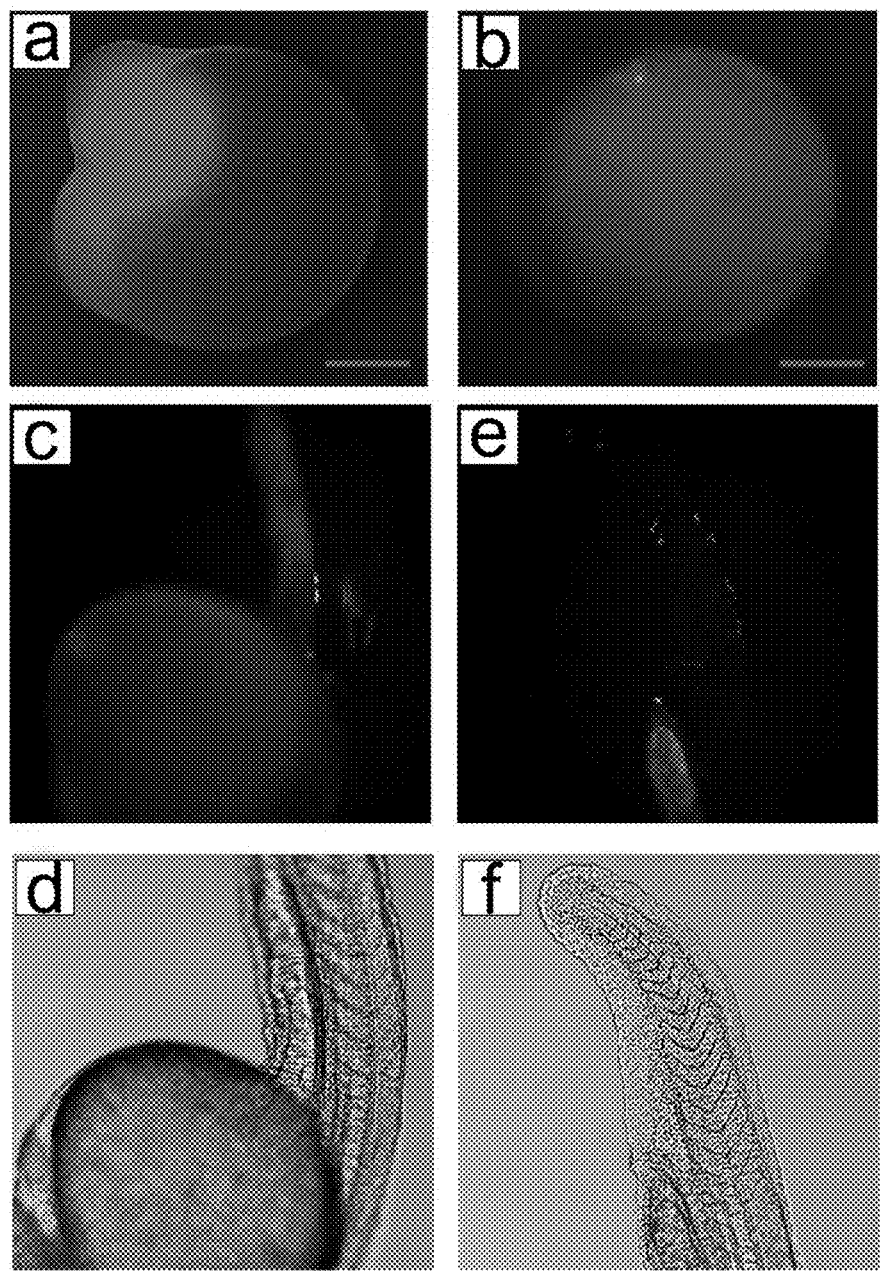
FIG. 7 shows an early 2-cell stage embryo premeabilized in the presence of exogenous streptavidin-conjugated quantum dots.

Now referring to FIG. 7, shown are a series of photographs as follows: (a) An early 2-cell stage embryo permeabilized in the presence of exogenous streptavidin-conjugated quantum dots. Quantum dot fluorescence was observed in the blastomere cells. (b) Just after the germ-ring stage, blastomere fluorescence was still observable. (c), (e) Fluorescence and (d), (f) bright field images of 24 hours post-fertilized larvae permeabilized at the early to mid-cleavage stage in the presence of plasmid DNA. Expression of the construct was observed along the gut, notochord, floor plate, somites and tail cells (c), (d), (e), and (f).

Thus, in an aspect, there is provided a method, apparatus and system for altering physical and chemical properties, chemical composition, ionize, remove, deplete, denature, and destroy drusen in its different classifications (e.g. retinal drusen, colloidal bodies of retina, basal laminar drusen, drusen of Bruch's membrane, cuticular drusen, adult-onset, grouped) deposits in human and animal retinas for age-related macular degeneration treatment.

In an embodiment, the system comprises: (a) a coherent ultrashort pulsed laser source or a ultrashort laser amplifier or a combination of both to produce a single or multiple femtosecond laser pulses of a preset temporal duration, energy, wavelength, spectral distribution, energy fluence, and power density; (b) Optically coupled and delivery to the ultrashort pulsed laser source or ultrashort laser amplifier or a combination of both, for delivering the femtosecond laser pulses through the cornea, manipulating, targeting within the retinal pigmented epithelium layer and or other deposits in the macula, and focusing of one or more femtosecond laser pulses with a predetermined amount of energy on drusen deposits at predetermined location in the retina; (c) Automated positioning and imaging module of drusen deposits relative to the focused laser pulse location; and A computer or manual controlled femtosecond laser 3D beam translators that moves the targeting laser focal spot to the drusen location for treatment; (d) Means of delivering the laser pulse to the drusen which can be a slit lamp, Fundos camera system, fiber optic laser delivery system, collection of focusing lenses, lens objectives, or direct free-space illumination; (e) Drusen imaging module that identifies the drusen deposits via multi wavelength spectral imaging or direct optical detection or recognition; and (f) Femtosecond pulse duration manipulator and selector for pulse temporal compression, spectral reshaping and pulse train slicing.

In an embodiment, the system further comprises a coherent laser source which can be a femtosecond laser oscillator, a femtosecond laser oscillator injected plus a femtosecond laser pulse amplifier, a cavity dumped femtosecond laser, a femtosecond diode pumped laser, a femtosecond optical parametric amplifier, a femtosecond optical parametric oscillator, a femtosecond semiconductor laser, femtosecond pulse fiber laser, or a femtosecond laser fiber laser plus a femtosecond pulse fiber amplifier.

In another embodiment, the laser pulse is delivered via an articulated arm, free space, or optical fibers to a slit lamp, Fundos camera system, fiber optic laser delivery system, collection of focusing lenses, lens objectives, or direct free-space illumination, and In another embodiment, the system further comprises a pulse selector, a pulse shaper, a pulse compressor, a pulse stretcher, a pulse picker, and corrective optics for delivering the optical laser radiation to the dursen.

In another embodiment, the system further comprises a 3D laser beam positioning system that is either manual or computer controlled.

In another embodiment, the system further comprises means to control pulses frequency and polarization.

In another embodiment, the system further comprises a module for controlling the beam shape having a cross section of a desired surface area (pulse spatial shape controller)

In another aspect, there is provided a method of irradiating extracellular macular deposits through a cornea of an eye utilizing laser pulses, comprising: generating laser pulses of between about 1 femtosecond to 1,000,000 femtoseconds in a wavelength range from about 200 nanometers to 30 micrometers at an optical energy in a range of about 0.001 nJ to 100 mJ per laser pulse; and irradiating the extracellular macular deposits with the laser pulses for a preset temporal duration, energy, wavelength, spectral distribution, energy fluence, and power density.

In an embodiment, the laser pulses are between about 1 femtosecond to 10,000 femtoseconds in a wavelength range from about 200 nanometers to 10 micrometers at an optical energy in a range of about 0.001 nJ to 100 mJ per laser pulse.

In another embodiment, the method further comprises targeting the extracellular macular deposits within a retinal pigmented epithelium layer, or within a mascula utilizing multi wavelength spectral imaging, or direct optical detection.

In another embodiment, the method further comprises automatically focussing the focal spot of the laser pulses on the extracellular macular deposits utilizing 3D beam translators.

In another embodiment, the method further comprises utilizing a femtosecond pulse duration manipulator and selector for pulse temporal compression, spectral reshaping and pulse train slicing.

In another embodiment, the method further comprises delivering the laser pulses to the extracellular macular deposits utilizing one or more of a femtosecond laser oscillator, a femtosecond laser oscillator with a femtosecond laser pulse amplifier, a cavity dumped femtosecond laser, a femtosecond diode pumped laser, a femtosecond optical parametric amplifier, a femtosecond optical parametric oscillator, a femtosecond semiconductor laser, a femtosecond pulse fiber laser, or a femtosecond laser fiber laser with a femtosecond pulse fiber amplifier.

In another embodiment, the extracellular macular deposits comprise one or more of retinal drusen, colloidal bodies of retina, basal laminar drusen, and drusen of Bruch's membrane.

In another embodiment, the method further comprises irradiating laser pulse is configured to ionize, remove, deplete, denature, and destroy the extracellular macular deposits without damaging the retinal pigmented epithelium cell membrane or mascula.

In another aspect, there is provided an apparatus for irradiating extracellular macular deposits through a cornea of an eye utilizing laser pulses, comprising: a laser source for generating laser pulses of between about 1 femtosecond to 1,000,000 femtoseconds in a wavelength range from about 200 nanometers to 30 micrometers at an optical energy in the range of about 0.001 nJ to 100 mJ per laser pulse; and a laser targeting module for irradiating the extracellular macular deposits with the laser pulses for a preset temporal duration, energy, wavelength, spectral distribution, energy fluence, and power density.

In an embodiment, the laser pulses are between about 1 femtosecond to 10,000 femtoseconds in a wavelength range from about 200 nanometers to 10 micrometers at an optical energy in the range of about 0.001 nJ to 100 mJ per laser pulse.

In another embodiment, the laser targeting module is adapted to target the extracellular macular deposits within a retinal pigmented epithelium layer, or within a mascula utilizing multi wavelength spectral imaging, or direct optical detection.

In another embodiment, the laser targeting module is adapted to utilize 3D beam translators to automatically focus the focal spot of the laser pulses on the extracellular macular deposits.

In another embodiment, the laser source further comprises a femtosecond pulse duration manipulator and selector for pulse temporal compression, spectral reshaping and pulse train slicing.

In another embodiment, the laser source is one or more of a femtosecond laser oscillator, a femtosecond laser oscillator with a femtosecond laser pulse amplifier, a cavity dumped femtosecond laser, a femtosecond diode pumped laser, a femtosecond optical parametric amplifier, a femtosecond optical parametric oscillator, a femtosecond semiconductor laser, a femtosecond pulse fiber laser, or a femtosecond laser fiber laser with a femtosecond pulse fiber amplifier.

In another embodiment, the extracellular macular deposits to be irradiated comprise one or more of retinal drusen, colloidal bodies of retina, basal laminar drusen, and drusen of Bruch's membrane.

In another embodiment, the irradiating laser pulse is configured to ionize, remove, deplete, denature, and destroy the extracellular macular deposits without damaging the retinal pigmented epithelium cell membrane or mascula.

In another embodiment, the laser pulse is delivered via an articulated arm, free space illumination, optical fibers to a slit lamp, a fundus camera system, or fiber optic laser delivery system.

In another embodiment, the apparatus further comprises one or more of a pulse selector, a pulse shaper, a pulse compressor, a pulse stretcher, a pulse picker, and corrective optics.

In another embodiment, the laser source is further adapted to control pulses frequency and polarization.

In another embodiment, the apparatus further comprises a pulsed spatial shape controller for controlling the shape of the pulsed laser to have a cross section of a desired surface area.

In another embodiment, the laser source is adapted to deliver simultaneous laser pulses at multiple wavelengths of spectral bandwidths anywhere within a range of 10 nm to 600 nm. While the above description provides examples of one or more embodiment and methods, it will be appreciated that other embodiments and methods may be within the scope of the present description as interpreted by one of skill in the art.

REFERENCES

[1] "About AMD" Internet: http://www.cnib.ca/en/your-eyes/eye-conditions/eyeconnect/AMD/About/Pages/default.aspx

[2] H. Kolb, R. Nelson, E. Fernandez, and B. Jones. "WEBVISION: The Organization of the Retina and Visual System" [On-Line] Available: http://webvision.med.utah.edu/

[3] M Plunkett, A. Hussain, and J. Marchall. "Retinal Regeneration," US Patent Application No. 20100049173 A1, Feb. 25, 2010.

[4] Retinal Rejuvenation Therapy: Ellex 2RT Media Kit, Ellex Medical Pty Ltd., Adelaide, SA, Australia, 2010, pp. 1-23

[5] H. Al-Hussaini et al. "Mature retinal epithelium cells are retained in the cell cycle and proliferate in vivo," Molecular Vision, vol. 14, pp. 1784-1791, October 2008.

[6] M. T. Flood, P. Gouras, and H. Kjeldbye. "Growth characteristics and ultrastructure of human retinal pigment epithelium in vitro," Investigative Ophthalmology and Visual Science, vol. 19(11), pp. 1309-1320, November 1980.

[7] A. M. Harman et al. "Development and aging of cell topography in the human retinal pigment epithelium" Investigative Opthalmology and Visual Science, vol. 38(10), pp. 2016-2026, September 1997.

[8] I. Kokkinopoulos et al. "Mature peripheral RPE cells have an intrinsic capacity to proliferate; a potential regulatory mechanism for age-related cell loss," PLOS One, vol. 6(4), pp. 1-10, April 2011.

[9] A. Vogel, at al., Mechanisms of femtosecond laser nanosurgery of cells and tissues, Applied Physics B 2005, 81

[10] V. Kohli, et al., Embryonic surgery using femtosecond laser pulses for the delivery of exogenous materials and the analysis of gene expression, SPIE, 2008, 6854

[11] V. Kohli et al., Morphological analysis of embryonic development following femtosecond laser manipulation, SPIE, 2008, 6854

[12] V. Kohli et al., From cells to embryos: The application of femtosecond laser pulses for altering cellular material in complex biological systems, SPIE, 2008, 6892

[13] M. Hu, at al., Gold nanostructures: Engineering their plasmonic properties for biomedical applications, Chemical Society Reviews 2006, 35

[14] H. Lubatschowski, et al., Medical applications for ultrafast laser pulses, RIKEN Review, 2003, 50

[15] A. Ovsianikov, et al., Three-dimensional photofabrication with femtosecond lasers for applications in photonics and biomedicine, Applied Surface Science, 2007, 253

[16] E. A. Wachter, et al., Photodynamic Therapy with Ultrafast Lasers, SPIE, 1999, 3616

[17] P. Ghosh, et al., Gold nanoparticles in delivery applications, Advanced Drug Delivery Reviews, 2008, 60

[18] J. Neev, et al., Ultrashort Pulse Lasers for Hard Tissue Ablation, IEEE Journal of Selected Topics in Quantum Electronics 1996, 2

The invention claimed is:

1. A method of irradiating extracellular macular deposits through a cornea of an eye utilizing laser pulses, comprising:
generating laser pulses of between about 1 femtosecond to 1,000,000 femtoseconds in a wavelength range from about 200 nanometers to 30 micrometers at an optical energy in a range of about 0.001 nJ to 100 mJ per laser pulse;
irradiating the extracellular macular deposits with the laser pulses for a preset temporal duration, energy, wavelength, spectral distribution, energy fluence, and power density; and
automatically focussing a focal spot of the laser pulses on the extracellular macular deposits below a top retinal tissue layer utilizing 3D beam translators;
whereby, the laser pulses are adapted to target and remove the extracellular macular deposits without ablating or creating an incision in the top retinal tissue layer.

2. The method of claim 1, wherein the laser pulses are between about 1 femtosecond to 10,000 femtoseconds in a wavelength range from about 200 nanometers to 10 micrometers at an optical energy in a range of about 0.001 nJ to 100 mJ per laser pulse.

3. The method of claim 1, further comprising targeting the extracellular macular deposits within a retinal pigmented epithelium layer or within a macula, utilizing multi wavelength spectral imaging, or direct optical detection.

4. The method of claim 1, further comprising utilizing a femtosecond pulse duration manipulator and selector for pulse temporal compression, spectral reshaping and pulse train slicing.

5. The method of claim 1, further comprising delivering the laser pulses to the extracellular macular deposits utilizing one or more of a femtosecond laser oscillator, a femtosecond laser oscillator with a femtosecond laser pulse amplifier, a cavity dumped femtosecond laser, a femtosecond diode pumped laser, a femtosecond optical parametric amplifier, a femtosecond optical parametric oscillator, a femtosecond semiconductor laser, a femtosecond pulse fiber laser, or a femtosecond laser fiber laser with a femtosecond pulse fiber amplifier.

6. The method of claim 1, wherein the extracellular macular deposits comprise one or more of retinal drusen, colloidal bodies of retina, basal laminar drusen, and drusen of Bruch's membrane.

7. The method of claim 6, wherein the irradiating laser pulse is configured to ionize, remove, deplete, denature, and destroy the extracellular macular deposits without damaging the top retinal tissue layer comprising retinal pigmented epithelium cell membrane or macula.

8. An apparatus for irradiating extracellular macular deposits through a cornea of an eye utilizing laser pulses, comprising:
a laser source for generating laser pulses of between about 1 femtosecond to 1,000,000 femtoseconds in a wavelength range from about 200 nanometers to 30 micrometers at an optical energy in the range of about 0.001 nJ to 100 mJ per laser pulse; and
a laser targeting module for irradiating the extracellular macular deposits with the laser pulses for a preset temporal duration, energy, wavelength, spectral distribution, energy fluence, and power density, wherein the laser targeting module is adapted to utilize 3D beam translators to automatically focus a focal spot of the laser pulses on the extracellular macular deposits below a top retinal tissue layer;
whereby, the laser pulses are adapted to target and remove the extracellular macular deposits without ablating or creating an incision in the top retinal tissue layer.

9. The apparatus of claim 8, wherein the laser pulses are between about 1 femtosecond to 10,000 femtoseconds in a wavelength range from about 200 nanometers to 10 micrometers at an optical energy in the range of about 0.001 nJ to 100 mJ per laser pulse.

10. The apparatus of claim 8, wherein the laser targeting module is adapted to target the extracellular macular deposits within a retinal pigmented epithelium layer or within a macula, utilizing multi wavelength spectral imaging, or direct optical detection.

11. The apparatus of claim 8, wherein the laser source further comprises a femtosecond pulse duration manipulator and selector for pulse temporal compression, spectral reshaping and pulse train slicing.

12. The apparatus of claim 8, wherein the laser source is one or more of a femtosecond laser oscillator, a femtosecond laser oscillator with a femtosecond laser pulse amplifier, a cavity dumped femtosecond laser, a femtosecond diode pumped laser, a femtosecond optical parametric amplifier, a femtosecond optical parametric oscillator, a femtosecond semiconductor laser, a femtosecond pulse fiber laser, or a femtosecond laser fiber laser with a femtosecond pulse fiber amplifier.

13. The apparatus of claim 8, wherein the extracellular macular deposits to be irradiated comprise one or more of retinal drusen, colloidal bodies of retina, basal laminar drusen, and drusen of Bruch's membrane.

14. The apparatus of claim 13, wherein the irradiating laser pulse is configured to ionize, remove, deplete, denature, and destroy the extracellular macular deposits without damaging the top retinal tissue layer comprising retinal pigmented epithelium cell membrane or macula.

15. The apparatus of claim 8, wherein the laser pulse is delivered via an articulated arm, free space illumination, optical fibers to a slit lamp, a fundus camera system, or fiber optic laser delivery system.

16. The apparatus of claim 8, further comprising one or more of a pulse selector, a pulse shaper, a pulse compressor, a pulse stretcher, a pulse picker, and corrective optics.

17. The apparatus of claim 8, wherein the laser source is further adapted to control pulses frequency and polarization.

18. The apparatus of claim 8, further comprising a pulsed spatial shape controller for controlling the shape of the pulsed laser to have a cross section of a desired surface area.

19. The apparatus of claim 8, wherein the laser source is adapted to deliver simultaneous laser pulses at multiple wavelengths of spectral bandwidths anywhere within a range of 10 nm to 600 nm.

* * * * *